(12) United States Patent
Hausen (10) Patent No.: US 7,875,029 B1
(45) Date of Patent: Jan. 25, 2011

(54) SURGICAL DEVICE SWITCHABLE BETWEEN CLIP APPLICATION AND COAGULATION MODES

(75) Inventor: Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 170 days.

(21) Appl. No.: 12/435,368

(22) Filed: May 4, 2009

(51) Int. Cl.
*A61B 18/14* (2006.01)
(52) U.S. Cl. .................. 606/52; 606/51; 606/142
(58) Field of Classification Search .......... 606/41, 606/45–52, 142, 143
See application file for complete search history.

(56) References Cited

U.S. PATENT DOCUMENTS

| | | | |
|---|---|---|---|
| 4,396,139 A | 8/1983 | Hall et al. | |
| 5,158,567 A | 10/1992 | Green | |
| 5,207,691 A * | 5/1993 | Nardella ................. | 606/142 |
| 5,389,098 A * | 2/1995 | Tsuruta et al. ............ | 606/41 |
| 5,403,312 A | 4/1995 | Yates et al. | |
| 5,624,452 A | 4/1997 | Yates | |
| 5,688,270 A | 11/1997 | Yates et al. | |
| 5,716,366 A | 2/1998 | Yates | |
| 5,735,848 A | 4/1998 | Yates et al. | |
| 5,792,094 A | 8/1998 | Stevens et al. | |
| 5,807,393 A * | 9/1998 | Williamson et al. ........ | 606/32 |
| 5,810,811 A | 9/1998 | Yates et al. | |
| 5,861,005 A | 1/1999 | Kontos | |
| 5,972,023 A | 10/1999 | Tanner et al. | |
| 6,149,660 A | 11/2000 | Laufer et al. | |
| 6,352,541 B1 | 3/2002 | Kienzle et al. | |
| H2037 H | 7/2002 | Yates et al. | |
| 6,482,224 B1 | 11/2002 | Michler et al. | |
| 6,537,289 B1 | 3/2003 | Kayan et al. | |
| 6,554,829 B2 * | 4/2003 | Schulze et al. ............. | 606/51 |
| 6,673,083 B1 | 1/2004 | Kayan et al. | |
| 6,695,854 B1 | 2/2004 | Kayan et al. | |
| 2005/0090834 A1 | 4/2005 | Chiang et al. | |
| 2005/0090843 A1 | 4/2005 | Bolduc | |
| 2005/0187613 A1 | 8/2005 | Bolduc et al. | |
| 2008/0147092 A1 | 6/2008 | Rogge et al. | |

* cited by examiner

*Primary Examiner*—Michael Peffley
(74) *Attorney, Agent, or Firm*—Brian A. Schar (57) ABSTRACT

One example of surgical apparatus for treating tissue may include an effector including at least two jaws movable toward one another, where the effector holds and is configured to deploy a of clips in a clip application mode, and where the jaws are configured to deliver energy to coagulate tissue in a coagulation mode, where said effector is switchable between clip application mode and coagulation mode. Another example of surgical apparatus for treating tissue may include an effector holding clips, and two fingers movable toward one another to close the clips one at a time, where each finger is a different pole of a bipolar coagulator. An exemplary method for treating tissue with a surgical apparatus may include placing the surgical apparatus adjacent to tissue at a location, selecting one of a plurality of operational modes of the surgical apparatus, where the operational modes include clip application mode and coagulation mode, and actuating the surgical apparatus according to the selected operational mode.

17 Claims, 9 Drawing Sheets

SURGICAL DEVICE SWITCHABLE BETWEEN CLIP APPLICATION AND COAGULATION MODES

FIELD OF THE INVENTION

The present invention relates generally to a surgical clip applier and a method for surgical clip application.

BACKGROUND

Surgical clip appliers have been utilized to overcome some of the difficulties associated with suturing. However, a large subset of clip appliers known in the art are single-use devices, capable of deploying only a single clip or set of clips at one time. To deploy another clip or set of clips, a new device must be utilized, or the device must be reloaded with another cartridge of clips. Where multiple clips must be placed at different locations in the body, such use of multiple tools is time consuming, expensive and wasteful. Some surgical clip appliers known in the art are capable of deploying multiple clips, one after the other, in different locations in the body. However, such tools are complex and bulky, and may be incapable of deploying clips properly sized to be useful in some minimally invasive surgical procedures.

Coagulation-based devices for dissecting tissue also are known and used in surgical procedures. These devices clamp tissue, deliver energy such as RF energy or ultrasound to tissue in order to cause coagulation to heat seal the tissue, then use a knife to cut the tissue. A surgeon may use such a device, for example, to separate side branches from a saphenous vein during endoscopic vein harvesting in preparation for coronary artery bypass graft (CABG) surgery. However, in the course of using a coagulation-based device, the surgeon may encounter blood vessels that are larger than a coagulation-based device can safely handle. Consequently, the surgeon must then set aside the coagulation device and switch to a separate clip applier. Switching between tools is time-consuming, expensive, and inconvenient, particularly in minimally-invasive, laparoscopic, or port-access surgical procedures, where the tissue to be dissected can be lost upon withdrawal of the tool such that the surgeon must spend time finding that tissue again upon the insertion of a different tool.

BRIEF DESCRIPTION OF THE DRAWINGS

The use of the same reference symbols in different figures indicates similar or identical items.

DETAILED DESCRIPTION

Clip Applier

Figure 1:
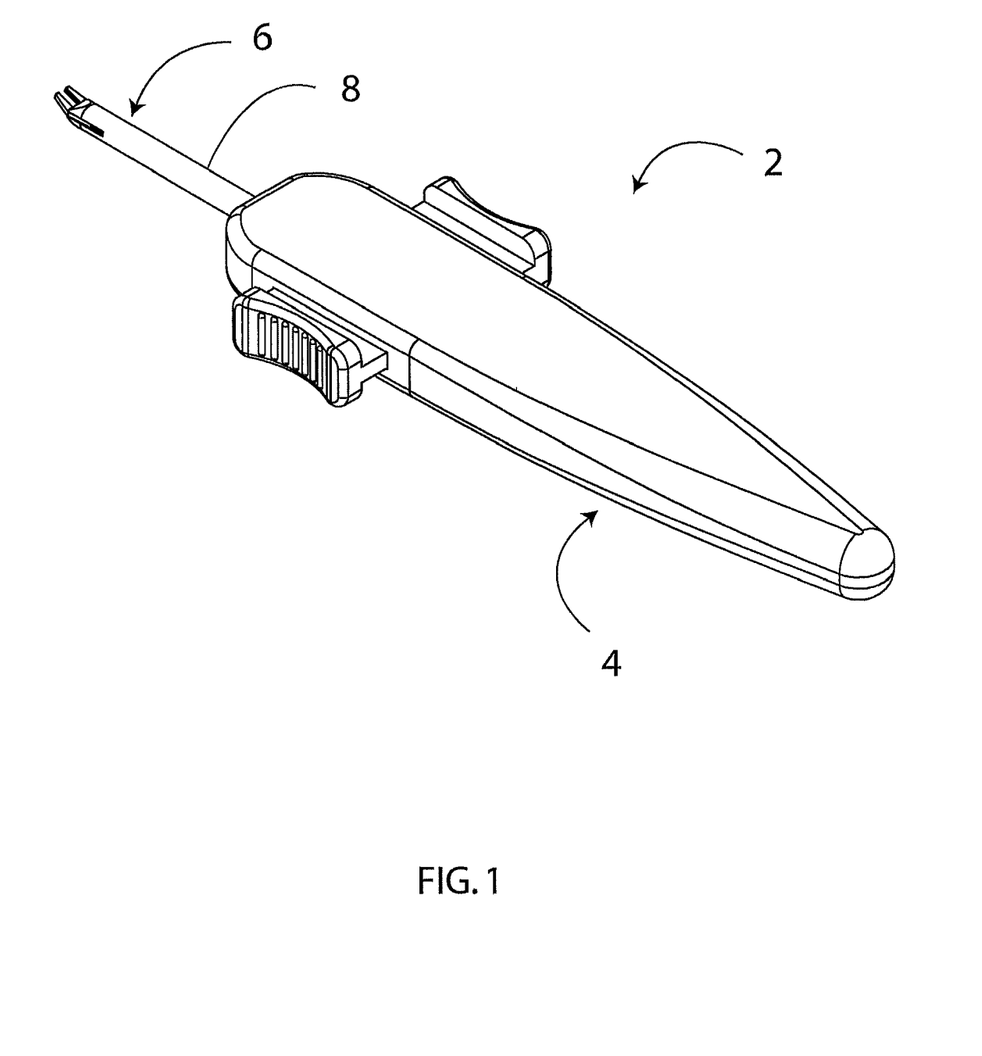
FIG. 1 is a perspective view of an exemplary surgical clip applier.

Referring to FIG. 1, a surgical clip applier 2 includes a handle 4 connected to an effector 6. With regard to the application of clips, the clip applier 2 may be substantially as described in U.S. patent application Ser. No. 12/370,576, filed on Feb. 12, 2009, which is hereby incorporated by reference in its entirety. The handle 4 may be connected directly to the effector 6, or may be connected to a shaft 8 that in turn is connected to the effector 6. The shaft 8 may be rigid, articulated or flexible. The handle 4 may have any suitable configuration, as described in greater detail below. The effector 6 may be sized to pass through an access port in a patient for use in a minimally-invasive surgical procedure. The effector 6 may be sized and shaped to allow it to be inserted through an access port in a patient of 5 mm in diameter or less. Alternately, the effector 6 may be sized and/or shaped differently. The effector 6 may be substantially rigid, substantially flexible, or a combination of both. The handle 4 may include one or more triggers, levers, knobs, buttons or other input features used to actuate and/or control the effector 6.

Figure 2:
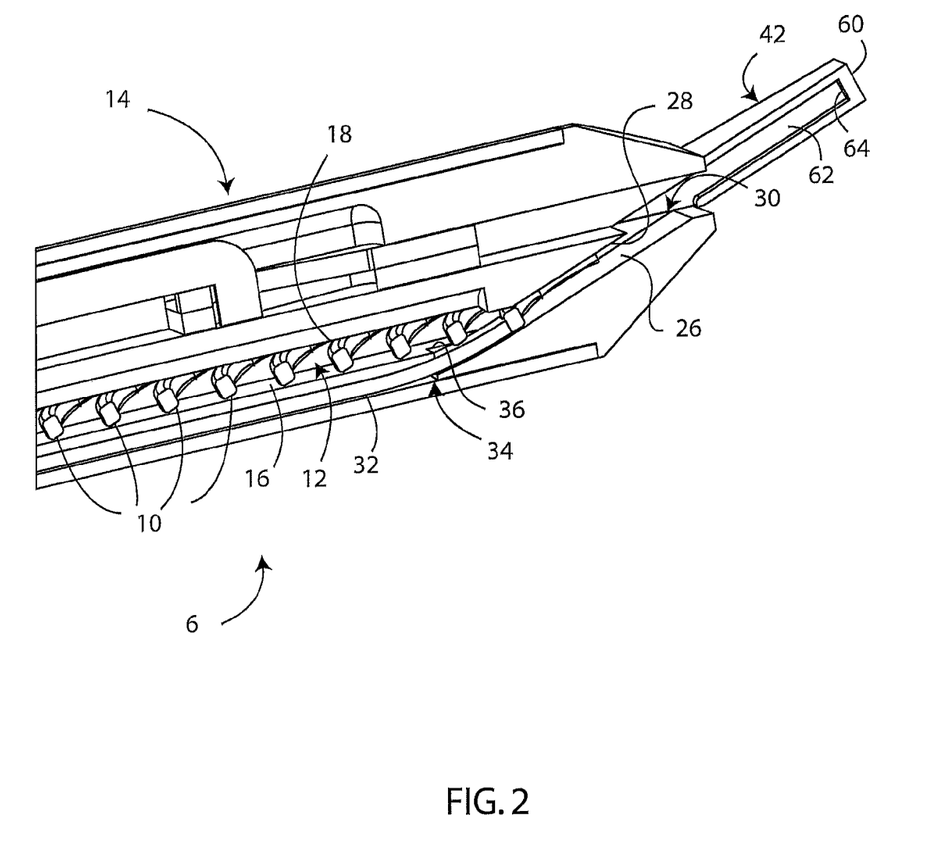
FIG. 2 is a cutaway perspective view of the distal end of an exemplary effector of the surgical clip applier of FIG. 1.

Referring to FIG. 2, the effector 6 may hold one or more clips 10 within a passage 12 in a housing 14. The housing 14 may be elongated longitudinally, and may have a longitudinal centerline. The passage 12 in the housing 14 may itself have a longitudinal centerline that is offset from and generally parallel to the longitudinal centerline of the housing 14. Alternately, the passage 12 may be located in and/or oriented within the housing 14 in any other suitable manner. The passage 12 may have a lower surface 16 and an upper surface 18. One or more clips 10 are located within the passage 12. The clips 10 may be oriented at an angle to the longitudinal centerline of the passage 12 and/or the longitudinal centerline of the housing 14. The clips 10 may be constrained within the passage 12 by the surfaces 16, 18, as well as the lateral surfaces of the passage 12. The clips 10 may be independent from one another, and placed adjacent to one another. Alternately, the clips 10 may be connected to or associated with one another in any suitable manner. As one example, the clips 10 may be coated with parylene such that they are held together as a single assembly, in order to facilitate manufacture of the clip applier 2. As another example, one or more clips 10 may be frangibly connected to a wire or backbone (not shown) from which each clip 10 may be sheared upon deployment, in order to facilitate manufacture of the clip applier 2.

Figure 2A:
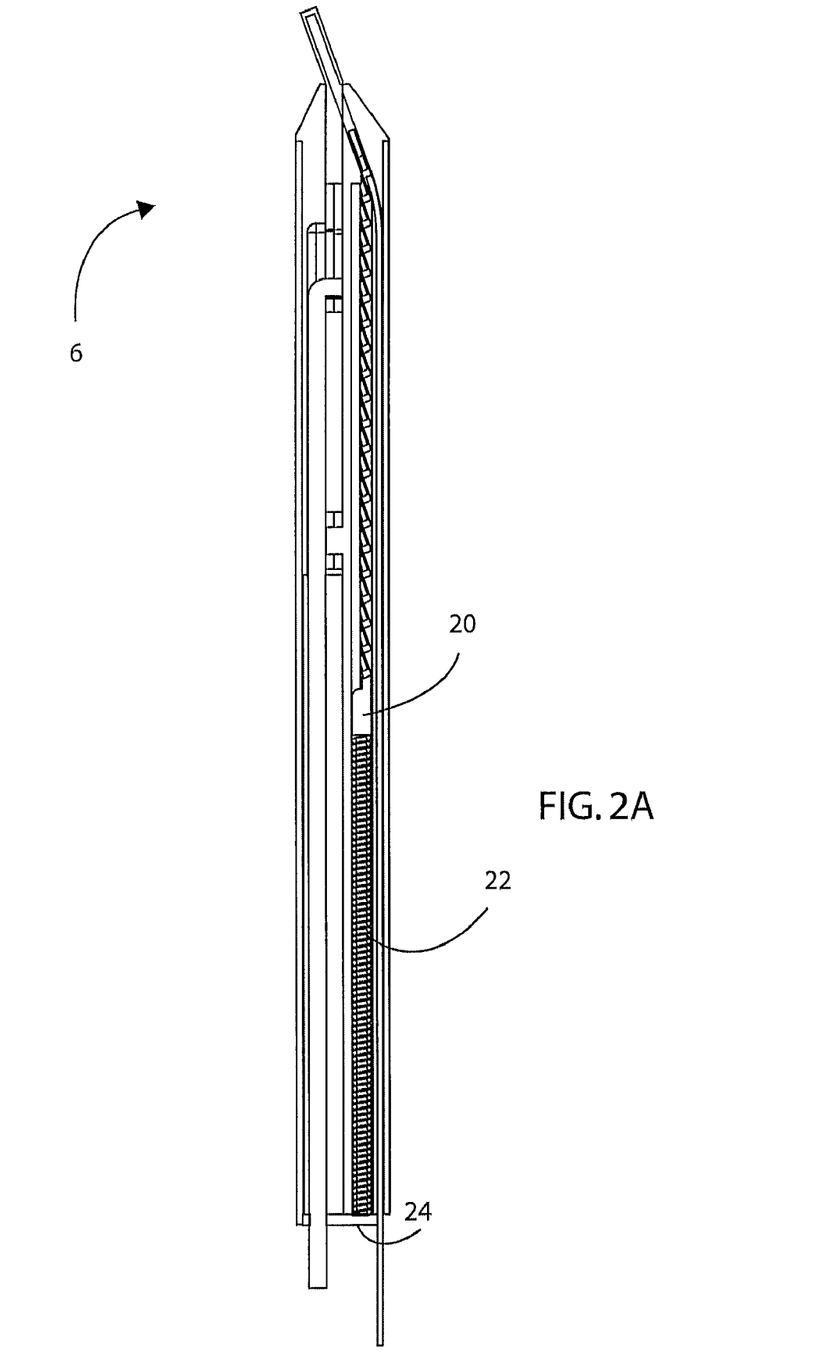
FIG. 2A is a side cutaway view of the exemplary effector of the surgical clip applier of FIG. 1.
Figure 3:
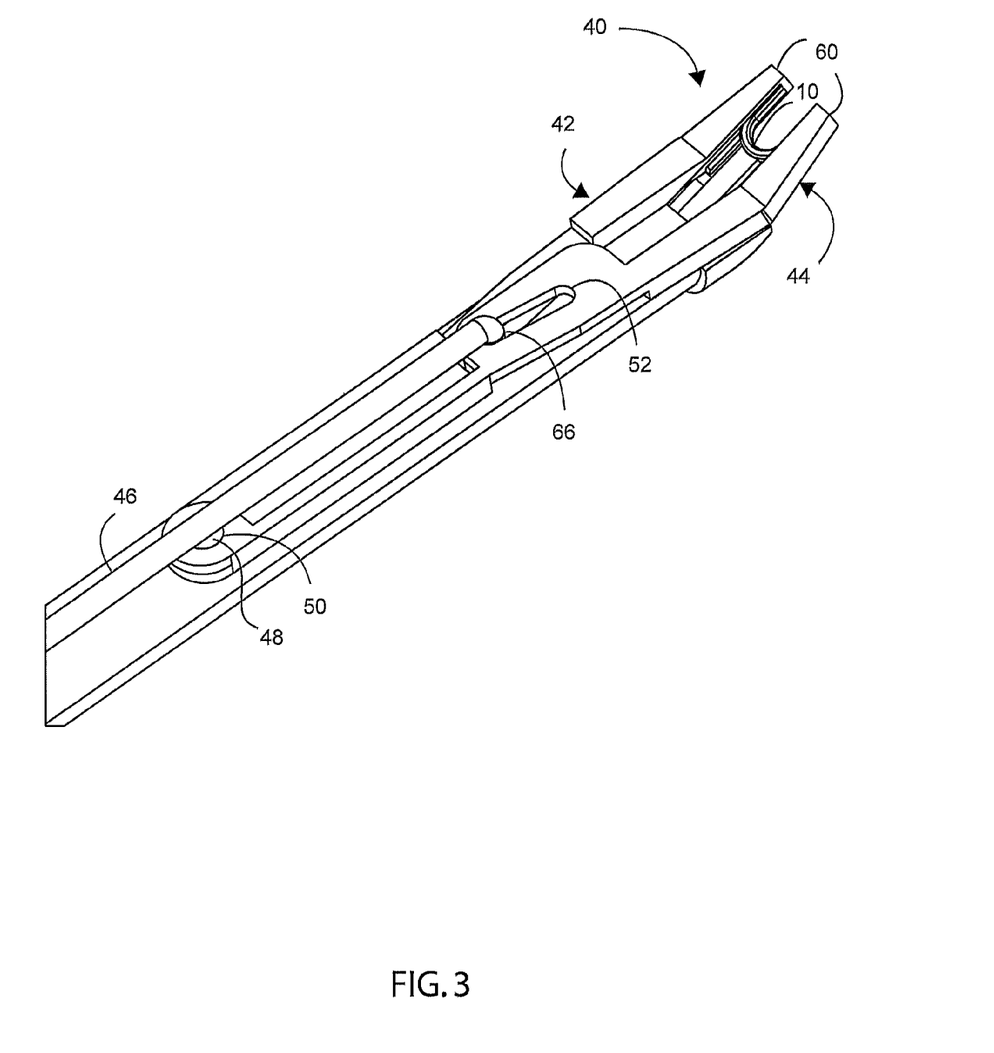
FIG. 3 is a perspective view of a portion of the distal end of the exemplary effector of the surgical stapler of FIG. 1, with a clip in ready position.

Referring also to FIG. 2A, a clip pusher 20 may be located in the passage 12, proximal to the clip or clips 10. The clip pusher 20 may contact the most proximal clip 10 in the passage 12, and exert a force on that most proximal clip 10 in the distal direction. The distal force may be transmitted from each clip 10 to the clip 10 distally next in line, such that the clip pusher 20 exerts a distal force on all of the clips 10. The clip pusher 20 may be biased distally, or may be selectively urged distally. Where the clip pusher 20 is biased distally, such bias may be provided by a compression spring 22, by a pneumatic force, by a magnetic or electromagnetic actuator, a solenoid, or any other suitable structure or mechanism. The distal end of the compression spring 22 may abut or may be fastened to the clip pusher 20, and the proximal end of the compression spring 22 may abut or be fixed to a wall 24 or other portion of the housing 14 such that the proximal end of the compression spring 22 is held in a substantially fixed location. However, the compression spring 22 may be arranged differently relative to the housing 14, if desired. Where the clip pusher 20 is selectively urged distally, the handle 4 may be used to control the timing of the application of distal force to the clip pusher 20, which may be applied by a compression spring 22, by a pneumatic force, by a magnetic or electromagnetic actuator, a solenoid, or any other suitable structure or mechanism.

A lower ramp 26 may be located at the distal end of the passage 12. The lower ramp 26 advantageously is oriented at the same angle to the longitudinal centerline of the housing 16 as the clip or clips 10. The distalmost clip 10 in the passage may be pressed against the ramp 26 by the compressive force applied to that clip 10 by the clip pusher 20. A upper ramp 28 may be generally parallel to the lower ramp 26, and spaced apart from the lower ramp 26 by a distance slightly greater than the thickness of the clip or clips 10. Friction between the distalmost clip 10 and the ramps 26, 28 holds the distalmost clip 10 in place. Optionally, a detent or other mechanism may be used to hold the distalmost clip in place. An opening 30 is located between the distal ends of the ramps 26, 28. Clips 10 are sequentially urged through that opening 30, as described in greater detail below.

A pusher 32 is slidable along a pusher slot 34 in the housing 14. The pusher 32 may be generally elongated, and may have a generally rectangular cross-section. Alternately, the pusher 32 may be shaped differently. The pusher slot 34 may be generally parallel to and underneath the passage 12. Alternately, the pusher slot 34 may be located and/or oriented differently. The distal end of the pusher slot 34 includes an aperture 36 connecting the pusher slot 34 to the passage 12. The aperture 36 is preferably oriented such that the distal end of the pusher 32 extends out of the aperture 36 onto the lower ramp 26. Alternately, the pusher slot 34 is omitted, and the pusher 32 is slidable along a trench or other feature in the housing 14.

Referring also to FIGS. 3-6, the effector 6 includes an actively-controlled crimper 40. The crimper 40 includes a first jaw 42, a second jaw 44, and a control arm 46. Each jaw 42, 44 may be substantially planar, and the jaws 42, 44 may be positioned such that the second jaw 44 rests on the upper surface of the first jaw 42. Alternately, at least one jaw 42, 44 may be shaped or oriented differently. The proximal end of each jaw 42, 44 may be configured to pivot about a post 48 within the housing 14, where the post 48 has a substantially fixed location within the housing 14. For example, the proximal end of each jaw 42, 44 may include a generally circular opening 50 that receives the post 48 therein. Moving distally to a middle portion of each jaw 42, 44, an angled control slot 52 is defined in each jaw 42, 44. The control slot 52 of each jaw 42, 44 is oriented such that the distal end of the control slot 52 is located laterally outward from the proximal end of the control slot 52. The control slot 52 of the first jaw 42 may be oriented laterally in the opposite direction as the control slot 52 of the second jaw 44. Moving distally, each jaw 42, 44 ends in a finger 60, where the fingers 60 are configured to receive a clip 10 therebetween. Each finger 60 may be angled relative to the longitudinal centerline of the effector 6 approximately the same amount as the lower ramp 26, and may extend outward from the opening 30 such that a clip 10 can slide smoothly along the lower ramp 26, out of the opening 30, and into the space between the fingers 60. The inner surface of each finger 60 may include a trench 62 defined therein. Each trench 62 may be sized to be substantially as wide as a clip 10. Each trench 62 may be deep enough such that the distal end 64 of each trench 62 acts as a stop, such that a clip 10 is advanced between the fingers 60 until the distal end of the clip 10 encounters the ends 64 of the trenches 62 in the fingers 60.

The arm 46 may extend generally parallel to the jaws 42 along at least part of its length. The distal tip 66 of the arm 46 is bent downward or otherwise configured to enter both control slots 52 of the jaws 42, 44. Initially, the distal tip 66 of the arm 46 is located at the proximal end of each slot 52, and the fingers 60 of the jaws 42, 44 are spaced apart from one another. Alternately, a feature 66 is located on the control arm 46 other than at its distal end, and extends downward into both control slots 52 of the jaws 42, 44.

The clips 10 may be generally U-shaped, or otherwise configured. Each clip 10 may lie substantially in a single plane. That is, each clip 10 is shaped such that a single plane extends through and substantially bisects the entire clip 10. Alternately, at least one clip 10 does not lie substantially in a single plane. The longitudinal and lateral dimensions of the clips 10 overall may both be substantially larger than the height of the clips 10. Alternately, the clips 10 may be sized differently. Advantageously, the clips 10 may be plastically deformable. That is, the clips 10 may undergo a permanent deformation when subjected to a stress exceeding its yield value. In other words, plastic deformation is deformation that remains after the load that caused it is removed, or that would remain if the load were removed. If so, the clips 10 may be fabricated from stainless steel, titanium or any other suitable plastically-deformable material. Alternately, the clips 10 may be elastically deformable. If so, the clips 10 may be fabricated from nickel-titanium alloy or any other suitable elastic or superelastic material. Each clip 10 may be fabricated from a single wire or other piece of material, having a rectangular, circular or other cross-section. However, the clips 10 may be fabricated in any suitable manner. The cross-section of each clip 10 may be substantially constant along the entire clip 10, or may vary at different locations along the clip 10. For example, the cross-sectional area of the clip 10 at certain locations may be less than at other locations, in order to promote bending in those locations having a lesser cross-sectional area. The cross-sectional shape of the clip 10 may be square, rectangular, circular, oval or any other suitable shape, and may be substantially constant along the entire clip 10 or vary at different locations along the clip 10.

Figure 7:
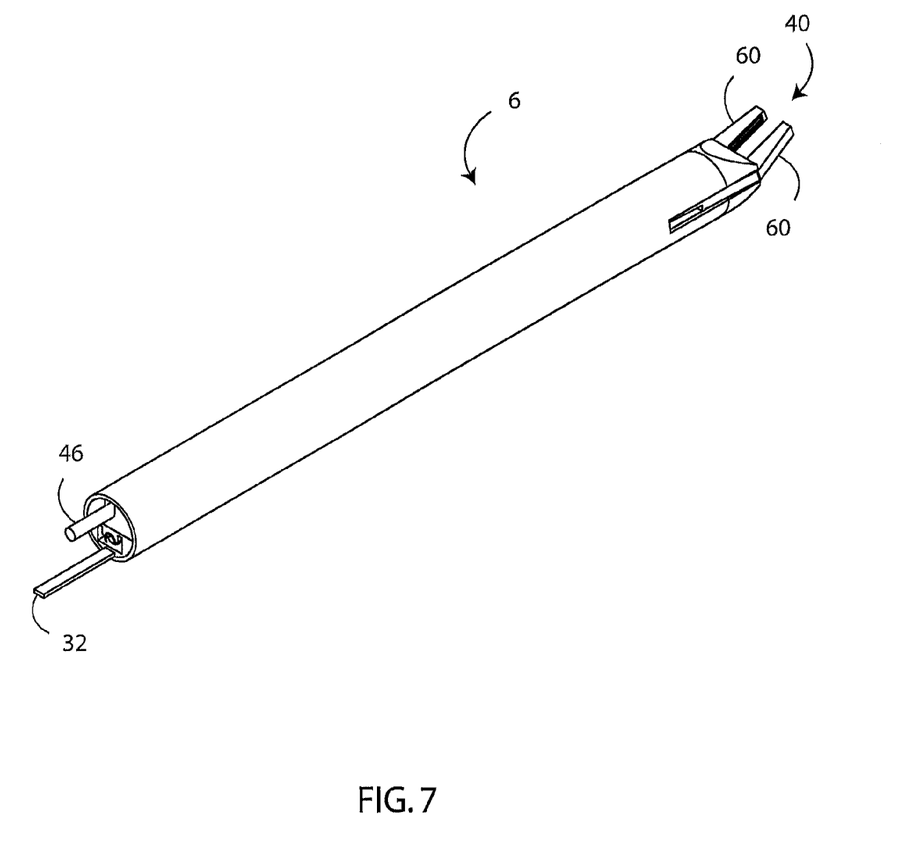
FIG. 7 is a perspective view of the exemplary effector of the surgical clip applier of FIG. 1.

The handle 4 may include any mechanism, mechanisms, structure or structures configured to actuate the effector 6. Referring to FIG. 7, the proximal end of the pusher 32 and the proximal end of the control arm 46 may extend proximally out of the effector 6. The handle 4 may be configured in any suitable manner to control the motion of the pusher 32 and control arm 46. As one example, the pusher 32 and/or control arm 46, or structures or mechanisms connected to them, may extend through the shaft 8 to the handle 4. The handle 4 may include any suitable mechanism or mechanisms that provide for control of the pusher 32 and control arm 46, and may include a source of stored energy for actuating the effector 6. The source of stored energy may be mechanical (such as a spring), electrical (such as a battery), pneumatic (such as a cylinder of pressurized gas) or any other suitable source of stored energy. The source of stored energy, its regulation, and its use in actuating an effector 6 may be as described in U.S. patent application Ser. No. 10/392,336, filed on Mar. 19, 2003, or U.S. patent application Ser. No. 11/054,265, filed on Feb. 9, 2005, which are herein incorporated by reference in their entirety. The handle 4 may instead, or also, include a connector or connectors suitable for receiving stored energy from an external source, such as a hose connected to a hospital utility source of pressurized gas or of vacuum, or an electrical cord connectable to a power source.

Alternately, the handle 4 may be omitted, and the effector 6 may be actuated directly by a surgical robot such as the DaVinci® surgical robot of Intuitive Surgical, Inc. of Sunnyvale, Calif. The shaft 8 may be utilized, if desired, or the effector 6 may be mounted directly on an arm of the surgical robot. The surgical robot may provide all energy needed to actuate the effector 6, and may directly control the actuation of the effector 6.

Optionally, the effector 6 may include a cutaway, trough, lumen, ring or other feature (not shown) to allow the effector 6 to follow a guidewire to a treatment site.

Hybrid Clip Applier

Figure 8:
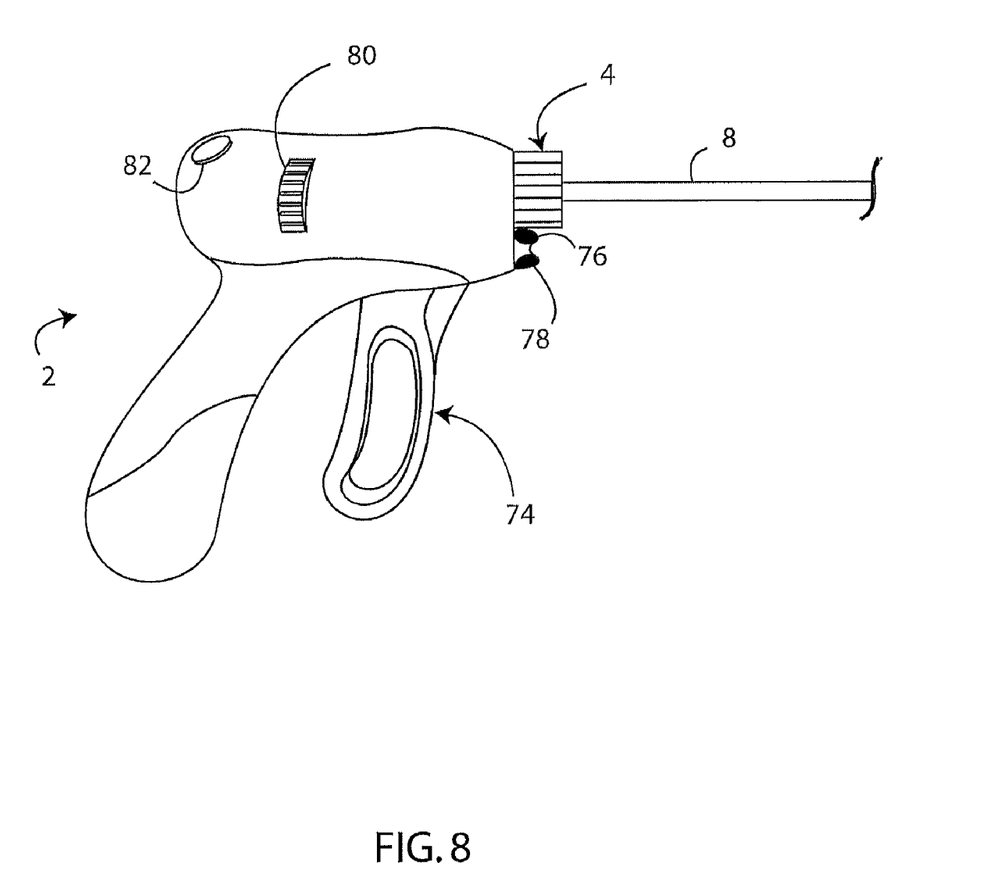
FIG. 8 is a side view of a handle of an exemplary hybrid clip applier.
Figure 9:
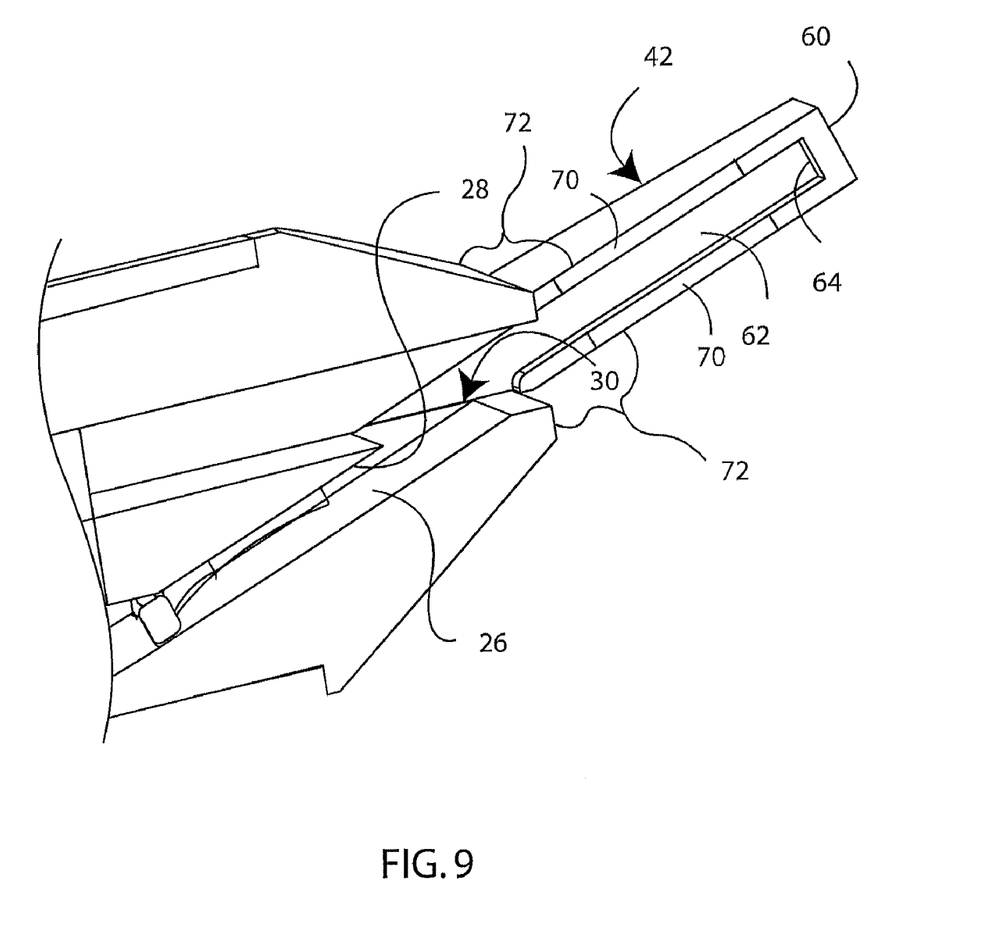
FIG. 9 is a detail perspective view of the end of one of the jaws of the exemplary hybrid clip applier of FIG. 8.

Referring to FIGS. 8-9, another embodiment of the clip applier 2 is configured to utilize one or more fingers 60 to coagulate tissue, as well as to close clips 10. The clip applier 2 is configured to either coagulate tissue in a coagulation mode or to deploy clips in a clip application mode. The two modes are mutually exclusive, to prevent electrical or other energy from traveling through a clip 10 that is being deployed or that has been deployed, which may result in injury to the patient and/or damage to the clip applier 2. Referring in particular to FIG. 9, at least one coagulation surface 70 may be located on an inner surface of at least one finger 60, facing the other finger 60. For example, at least one coagulation surface 70 may be located on an inner surface of at least one finger 60, above and/or below the trench 62 defined in that finger 60. As another example, at least one coagulation surface 70 may be located on an inner surface of at least one finger 60, distal to the trench 62 defined in that finger 60. Each coagulation surface 70 may be oriented generally longitudinally along the corresponding finger 60. Alternately, the entire inner surface 16 of the finger 60 may be a coagulation surface 70.

Each coagulation surface 70 is connected to an energy source in the handle 4 in any appropriate manner. For example, one or more wires 72 or waveguides may extend from a coagulation surface 70 through the shaft 8 to the energy source in the handle 4. The energy source connected to each coagulation surface 70 may be different from the energy source used to deploy clips 10, where such an energy source is utilized to deploy clips 10. For example, the handle 4 may include a cylinder of pressurized gas, a spring, or other source of stored energy used to deploy clips 10, and a connection to an electric power source for actuating the coagulation surfaces 70. The energy source connected to each coagulation surface 70 instead may be the same as the energy source used to deploy clips 10. Alternately, the energy source is not in the handle 4, but rather is external to the clip applier 2, such that energy passes from outside the clip applier 2 through the handle 4 to the coagulation surfaces 70 via a wire, wires, waveguide or waveguides 72, or such that energy passes from a source outside the clip applier 2 directly to the coagulation surfaces 70 via a wire, wires, waveguide or waveguides 72.

Each coagulation surface 70 may be configured in any suitable manner to deliver RF energy, ultrasound, heat, electricity or any other kind of energy to tissue. For example, at least one coagulation surface 70 may be a complete mechanism or other device configured to convert electrical or other energy into a different kind of energy suitable for causing coagulation. Such mechanisms and devices are known in the art. Each coagulation surface 70 may be a pole of a bipolar coagulator, or each may be unipolar. Bipolar cutting and coagulation is known in the art, and is described in, for example, U.S. Pat. No. 5,281,216 to Klicek, which is hereby incorporated by reference in its entirety. Advantageously, the coagulation surface or surfaces 70 on one finger 60 form one pole, and the coagulation surface or surfaces 70 on the other finger 60 form the other pole. Alternately, where multiple coagulation surfaces 70 are provided on at least one finger 60, at least one of those coagulation surfaces 70 has a different pole than at least one other coagulation surface 70 on that finger 60.

The clip applier 2 may be configured to deploy clips 10 or to apply energy to the coagulation surfaces 70, based on the selection of the user. Referring also to FIG. 9, as one example, the handle 4 may include a trigger 74 used for deploying clips 10 and a switch 76 for actuating the coagulating surfaces 70. Alternately, the switch 76 may be located elsewhere than the handle 4, and be connected to the clip applier 2 in any suitable manner. For example, the switch 76 may be a foot pedal connected electrically to the coagulation surfaces 70, whether via the handle 4 or directly to the coagulation surfaces 70 via the wires or waveguides 72. Such a switch 76 may be mechanical, electrical, a combination thereof, or a different kind of switch. Optionally, motion of the switch 76 may physically lock out the clips 10 from firing, such as by moving a tab into engagement with the trigger 74 to prevent actuation of the trigger 74. Alternately, a separate lock 78 may be provided on the handle 4, where that lock 78 is actuated (optionally or as an affirmative requirement) to lock out the clips 10 from firing prior to application of energy to the actuation surfaces. Alternately, the switch 76 is used to toggle between clip application mode and coagulation mode, and the trigger 74 is then used to actuate the clip applier 2 in each mode. Alternately, a master switch 82 is provided for toggling between clip application mode and coagulation mode, after which the trigger 74 is used to deploy clips 10 or the switch 76 is used to deliver energy to the coagulation surfaces 70. Alternately, the handle 8 may include any other features that allow the user to selectively deploy staples and coagulate tissue. Alternately, the clip applicator 2 may be configured to deploy clips 10 and apply energy to the coagulation surfaces 70 at the same time, either at the selection of the user, or as the only mode of operation of the clip applier 2. Alternately, the clip applier 2 may automatically toggle between clip application mode and coagulation mode based on feedback from compression of the tissue between the fingers 60, such that the user does not select the mode of operation of the clip applier 2.

The handle 4 may include a dial 80 for rotating the shaft 8 relative to the handle 4. The shaft 8 may extend into the handle 4, and the dial 80 may be directly fixed to the shaft 8, such that rotation of the dial 80 causes rotation of the shaft 8. The dial 80 may extend through an opening in the surface of the handle 4. Alternately, at least one gear is interposed between the dial 80 and the shaft 8. In this way, the user can rotate the shaft 8 and thus the end effector 6 relative to the handle 4, such that the user need not rotate the entire clip applier 2 to properly orient the effector 6 relative to tissue to be treated.

Figure 4:
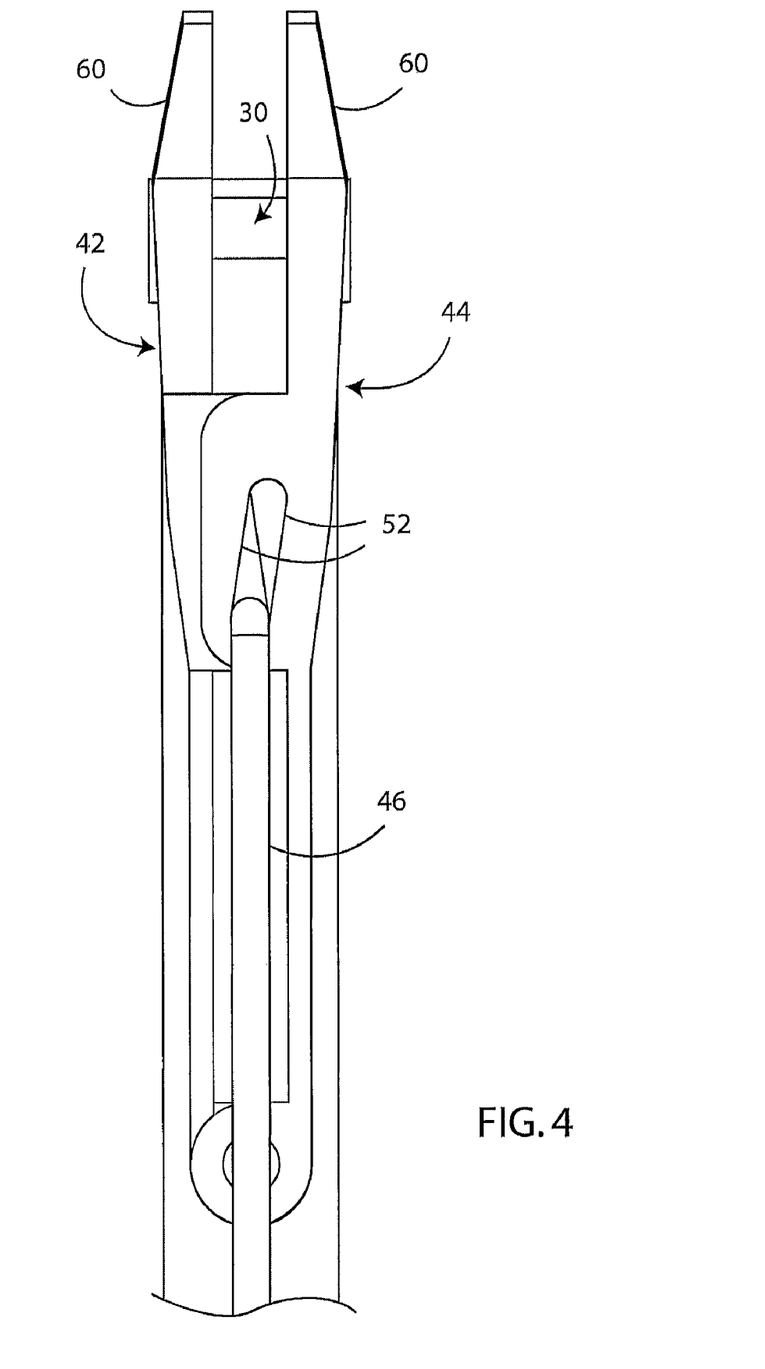
FIG. 4 is a top view of the distal end of the exemplary effector of the surgical stapler of FIG. 1, with the jaws open.
Figure 5:
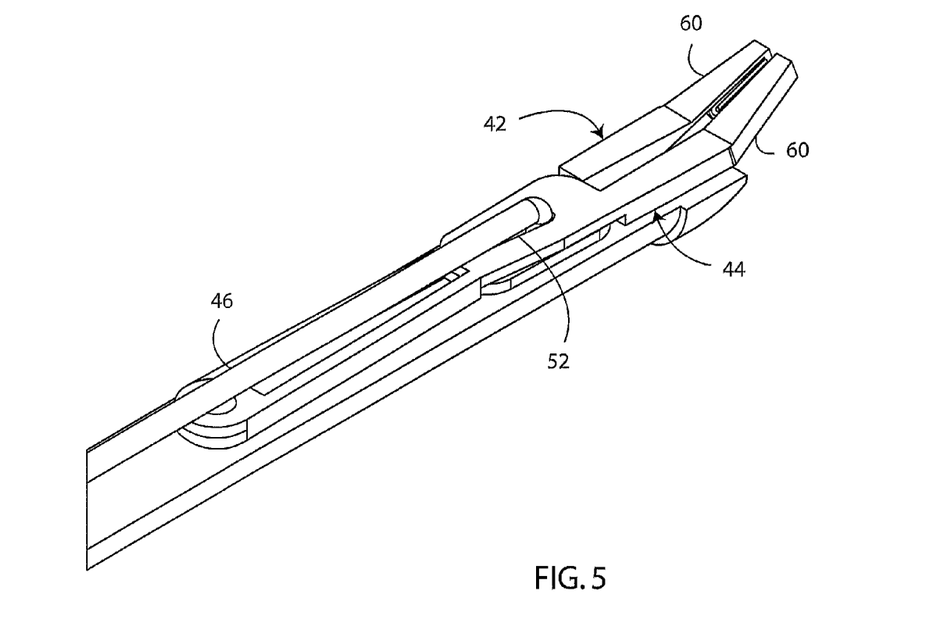
FIG. 5 is a perspective view of a portion of the distal end of the exemplary effector of the surgical stapler of FIG. 1, with a closed clip between the jaws.
Figure 6:
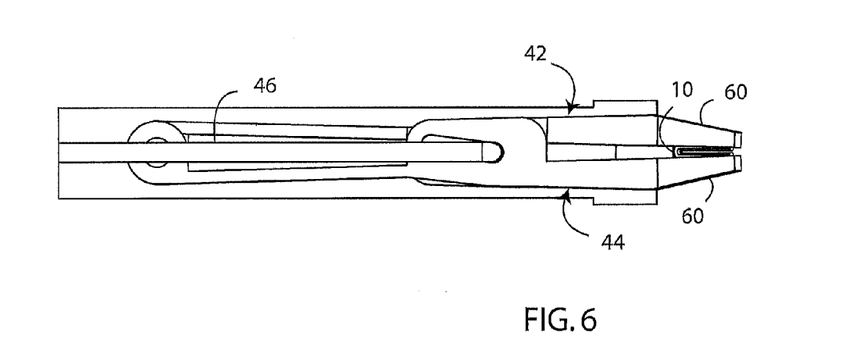
FIG. 6 is a top view of a portion of the distal end of the exemplary effector of the surgical stapler of FIG. 1, with a closed clip between the jaws.

As another example of a clip applier 2, referring to FIG. 4, each jaw 42, 44 may be conductive and may be a different pole of a bipolar coagulating system. Consequently, the fingers 60 at the ends of the jaws 42, 44 are different poles of a bipolar coagulating system. Energy may be transmitted to the jaws 42, 44 in substantially the same manner described above in which energy is transmitted to discrete coagulation surfaces 70, such as through wires or waveguides 72. Where the jaws 42, 44 form separate poles, an insulator or dielectric may be interposed between them within the effector 6, in order to prevent unintended energy flow between the jaws 42, 44. Further, the post 48 and the arm 46 are advantageously nonconductive for the same reason. The jaws 42, 44 may be actuated to coagulate tissue in substantially the same manner described above in which the coagulation surfaces 70 are actuated.

Operation

The operation of the clip applier 2 is described with regard to a generic surgical procedure. The clip applier 2 may be used in the course of any suitable surgical procedure, whether that surgical procedure is minimally-invasive or open, and whether the clip applier 2 is configured for manual or robotic actuation. For example, the surgical stapler 2 may be used to staple wounds or incisions in the skin together, for cardiac surgery, for hernia repair, for abdominal wall closure, for anti-reflux or other bariatric procedures, for intestinal repair, for dura mater surgery or other brain surgery, for aneurysm closure, for anastomosis, or for any other suitable medical use.

The distal end of the effector 6 may be placed in proximity to the tissue to be clipped. For example, the fingers 60 may be placed around a blood vessel. For clarity in describing the operation of the stapler 2, that tissue is not shown in the figures. Referring to FIGS. 2 and 4, the effector 6 is in an initial state. In the initial state, the fingers 60 are spaced apart from one another in an open configuration, prepared to receive a clip 10. The user then actuates the handle 4 and/or other component of the clip applier 2 to begin the deployment sequence. As described above, the handle 4 or other mechanism controls the motion of the components of the effector 6 in any suitable manner. First, the pusher 32 is advanced distally. As the pusher 32 advances, it contacts the proximal surface of the distalmost clip 10, then pushes that clip along the lower ramp 26 and through the opening 30. As the clip 10 moves through the opening 30, the lateral surfaces of the clip 10 enter the trenches 62 of the fingers 60, such that the fingers 60 can effectively hold the clip 10 therebetween. Motion of the clip 10 ceases when the pusher 32 ceases its distal motion, or when the distal end of the clip 10 encounters the distal end 64 of at least one trench 62. The clip 10 is thereby in position for placement on tissue. This position of the clip 10 may be referred to as the "ready position." The clip 10 may be placed around a blood vessel, onto tissue, or in any other suitable position before or after the clip 10 has reached the ready position.

The control arm 46 is then actuated to move distally; advantageously, the control arm 46 also moves substantially linearly. As the control arm 46 moves distally, the distal tip 66 of the control arm 46 moves distally as well. The distal tip 66 is located within the control slots 52 of the jaws 42, 44. As that distal tip 66 moves distally along a generally straight line, it encounters the inner surface of each angled control slot 52, thereby causing each jaw 42, 44 to move inward such as by rotating about the post 48. Thus, as the distal tip 66 moves distally, the fingers 60 move closer together, closing the clip 10. The distal tip 66 may travel all the way to the distal end of at least one control slot 52, or may be controlled by the handle 4 to move a shorter distance along at least one control slot 52. The distal tip 66 moves distally until the clip 10 is completely closed. After that deployment, the distal tip 66 is moved proximally, causing the fingers 60 to move apart and release the clip 10. The control arm 46 is moved proximally until the jaws 42, 44 return to their initial, open position in which the fingers 60 can receive another clip 10 between them. The jaws 42, 44 may be actively controlled at all times. "Active control" means that the opening and closing of the jaws 42 is controlled solely by the control arm 46, and is not dependent on or responsive to other input, such as contact between one or more of the fingers 60 and tissue. Alternately, the jaws 42, 44 may be otherwise controlled.

The pusher 32 is also moved proximally to its initial position. This motion may occur at any time after the clip 10 has been pushed into its ready position between the fingers 60. For example, the pusher 32 may move proximally before, during or after the distal tip 66 of the control arm 46 moves distally to close the clip 10 between the fingers 60. The clip pusher 20 may apply a compressive force collectively to all of the clips 10 in the passage before, during and after each distalmost clip 10 is urged into the ready position. As a result, as the pusher 32 moves proximally, the distalmost remaining clip 10 in the passage 12 is urged distally against the pusher 32. When the distal tip of the pusher 32 moves beneath the distalmost remaining clip 10, all of the clips 10 advance in the passage 12, such that the distalmost remaining clip 10 is pushed against the lower ramp 26. Thus, the clips 10 may be advanced without the need for a belt, carrier or other mechanism to engage them each individually and separately and move them distally. The pusher 32 may then cease its proximal motion. At the time the pusher 32 ceases to move proximally, the distal end of the pusher 32 may be located in the passage 12, or may be located in the pusher slot 34. At this time, the effector 6 is ready for another actuation at any other suitable location in the patient.

Operation—Hybrid Clip Applier

The clip applier 2 with both clip application and coagulation modes is actuated substantially as described above with regard to clip application. Where a dial 80 is provided, the dial 80 may be rotated to orient the shaft 8 and thus the effector 6 in the desired position. Depending on the particular control scheme of the clip applier 2, the trigger 74 is simply squeezed. Alternately, the master switch 82 is actuated to select clip application mode prior to squeezing the trigger 74. Alternately, any other suitable control or controls may be used to deploy one or more clips 10. If the clip applier 2 is set to coagulation mode, then the trigger 74 may be locked out as described above until clip application mode is selected.

In order to actuate the coagulation surfaces 70, the clip applicator 2 is placed in coagulation mode. This may be done in any suitable manner, as set forth above. As one example, the switch 76 is simply depressed, and energy is applied to the coagulation surfaces 70. The fingers 60 may be moved toward one another to compress tissue therebetween as a consequence of actuating the switch 76. Alternately, the fingers 60 may be moved together by a partial squeeze of the trigger 74 sufficient to close the jaws 42, 44 toward one another, where motion of a clip 10 between the jaws 42, 44 is locked out in any suitable manner. Energy is transmitted to the coagulation surfaces 70 via the wires or waveguides 72, causing the tissue between the fingers that is in contact with the coagulation surfaces 70 to coagulate and seal. The energy transmitted to the coagulation surfaces 70 may also cut through the tissue between the fingers 60, such that application of energy to the coagulation surfaces 70 both seals and cuts tissue. The effector 6 is then moved away from the tissue. The user can then reposition the effector 6 at a different location in the patient to treat different tissue, whether than location is immediately adjacent to the previous location, or at a different location in the body altogether. The clip applier 2 can thus be used repeatedly in the patient to treat tissue at multiple surgical sites, both with clips and with coagulation. The user may continue in this manner until the clips are exhausted or until the treatment of tissue in the body is complete. In this way, the time and material needed to treat tissue within the patient may be reduced compared to conventional medical devices.

The terms "upper," "lower," "upward," "downward," "up," "down," "below," "above" and the like are used solely for convenience in this document; such terms refer to directions on the printed page and do not limit the orientation of the clip applier 2 as a whole, or of the handle 4, effector 6 and/or shaft 8, in use. While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. Surgical apparatus for treating tissue, comprising:
    an effector including at least two jaws movable toward one another;
    wherein said effector holds and is configured to deploy a plurality of clips in a clip application mode; and
    wherein said jaws are configured to deliver energy to coagulate tissue in a coagulation mode;
    wherein said effector is switchable between clip application mode and coagulation mode; and
    wherein said clip application mode and said coagulation mode are mutually exclusive, such that a single actuation of said effector causes said effector to perform in only one said mode.

2. The surgical apparatus of claim 1, incorporating by reference all of the elements of that claim; wherein each said jaw is one pole of a bipolar coagulator.

3. The surgical apparatus of claim 1, incorporating by reference all of the elements of that claim; wherein each jaw includes at least one finger extending therefrom, wherein said fingers are movable toward one another to serially compress clips therebetween.

4. The surgical apparatus of claim 3, incorporating by reference all of the elements of that claim; further comprising at least one coagulation surface positioned on each said finger.

5. The surgical apparatus of claim 1, incorporating by reference all of the elements of that claim; further comprising at least one wire connected to each coagulation surface whereby energy is delivered to said coagulation surface.

6. The surgical apparatus of claim 1, incorporating by reference all of the elements of that claim; further comprising a handle connected to said effector, said handle including a master switch, wherein said master switch switches said effector between clip application mode and coagulation mode.

7. The surgical apparatus of claim 1, incorporating by reference all of the elements of that claim; further comprising a trigger connected to said handle, said trigger actuable to cause said effector to deploy one said clip at a time.

8. The surgical apparatus of claim 1, incorporating by reference all of the elements of that claim; further comprising a switch connected to said handle, said switch actuable to deliver energy to said jaws to coagulate tissue.

9. The surgical apparatus of claim 8, incorporating by reference all of the elements of that claim; further comprising a lock connected to said handle, wherein said switch is not actuable until said lock is engaged.

10. The surgical apparatus of claim 1, incorporating by reference all of the elements of that claim; further comprising
    a handle,
    a shaft attached to said effector and rotatably coupled to said handle; and
    a dial in said handle, said dial coupled to said shaft, whereby rotation of said dial rotates said shaft relative to said handle.

11. A method for treating tissue with a surgical apparatus, comprising:
    placing the surgical apparatus adjacent to tissue at a location;
    selecting one of a plurality of operational modes of the surgical apparatus, wherein said operational modes include clip application mode and coagulation mode; and
    actuating said surgical apparatus according to the operational mode selected in said selecting; wherein said actuating causes said effector to perform only one of said clip application mode and said coagulation mode.

12. The method of claim 11, incorporating by reference all of the elements of that claim; further comprising placing said surgical apparatus adjacent to tissue at a different location, and repeating said selecting and said actuating.

13. The method of claim 11, incorporating by reference all of the elements of that claim; wherein each said operational mode is actuated by a different actuator on the surgical apparatus.

14. The method of claim 11, incorporating by reference all of the elements of that claim; further comprising, after said selecting one of a plurality of operational modes, locking out the remainder of said operational modes.

15. The method of claim 11, incorporating by reference all of the elements of that claim; wherein said coagulation mode is bipolar coagulation.

16. The method of claim 11, incorporating by reference all of the elements of that claim; wherein said actuating includes compressing tissue with said surgical apparatus.

17. The method of claim 11, incorporating by reference all of the elements of that claim; wherein said selecting is performed after said placing.

* * * * *